United States Patent [19]

Frommer et al.

[11] B 3,995,026
[45] Nov. 30, 1976

[54] AMYLASE INHIBITOR

[75] Inventors: Werner Frommer; Walter Puls; Delf Schmidt, all of Wuppertal, Germany

[73] Assignee: Bayer Aktiengesellschaft, Leverkusen, Germany

[22] Filed: June 24, 1974

[21] Appl. No.: 482,660

[44] Published under the second Trial Voluntary Protest Program on February 10, 1976 as document No. B 482,660.

Related U.S. Application Data

[62] Division of Ser. No. 336,687, Feb. 28, 1973, Pat. No. 3,855,066.

[30] Foreign Application Priority Data

Mar. 1, 1972 Germany............................ 2209833

[52] U.S. Cl................................. 424/115; 195/80 R
[51] Int. Cl.²......................................... A61K 35/00
[58] Field of Search....................... 424/115; 195/80

Primary Examiner—Jerome D. Goldberg
Attorney, Agent, or Firm—Depaoli & O'Brien

[57] ABSTRACT

The invention relates to an amylase inhibitor for glycoside-hydrolases derived from a new strain of microorganism, mutants and variants thereof, of the order Actinomycetales, means for their production comprising cultivation of the new strain of the order Actinomycetales, mutants and variants thereof, in appropriate nutrient solutions under conditions most favorable to growth and production of said amylase inhibitor and recovering an amylase inhibitor from culture broths of said nutrient solutions and said new strain of microorganism, mutants and variants thereof, of the order Actinomycetales as well as the use of said enzyme inhibitor in pharmaceutically acceptable therapeutic compositions suitable for use in the treatment and relief of conditions indicative of obesity, diabetes, pre-diabetes, gastritis, gastric and duodenal ulcers, hyperlippidemia (atheriosclerosis) and the like. The invention also contemplates the provision of methods of inhibiting the reaction of carbohydrates and glycoside-hydrolase enzymes, and particularly carbohydrate-splitting glycoside-hydrolase enzymes of the digestive tract by means of conducting said reaction of said carbohydrates and glycoside-hydrolase enzyme in the presence of a glycoside-hydrolase enzyme derived from a new strain, mutants and variants thereof, of the order Actinomycetales. The invention further contemplates the provision of method for the treatment of indications of the group consisting of obesity, adipose, hyperlippidemia (atheriosclerosis), diabetes, pre-diabetes, gastritis, gastric ulcer, duodenal ulcer and dental caries induced by the action of glycoside-hydrolase enzymes and carbohydrates which comprises employing an enzyme inhibitor for glycoside-hydrolase enzymes produced by a new strain of microorganism of the order Actinomycetales of the family Actinoplanaceae.

1 Claim, No Drawings

AMYLASE INHIBITOR

This is a division of application Ser. No. 336,687, filed Feb. 28, 1973. The original patent application, filed Feb. 28, 1973 as Ser. No. 336,687, is now U.S. Pat. No. 3,855,066.

BACKGROUND OF THE INVENTION

It is known that in animals and man, after the intake of starchy foodstuffs and beverages, hyperglycaemias arise which are caused by a rapid splitting of the starch by amylases of the digestive tract according to the following equation:

Starch 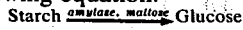 Glucose

These hyperglycaemias are particularly strong and long-lasting with diabetics. With adipose subjects the alimentary hyperglycaemia frequently causes a particularly strong insulin secretion which in turn leads to increased fat synthesis and reduced fat degradation. Following such a hyperglycaemia, a hypoglycaemia frequently occurs even with adipose persons of sound metabolism, as a result of hyperinsulinaemia. It is known that both hypoglycaemia and foodstuff sludge remaining in the stomach assist the production of gastric juice which in turn causes, or favors, the development of a gastritis, a duodenal ulcer or a gastric ulcer.

Accordingly, in the treatment of conditions in which there is an indication of obesity, adipose, hyperlippidemia (atheriosclerosis), diabetes, pre-diabetes, gastritis, gastric ulcer, duodenal ulcer, and/or caries, it is necessary that such glycoside-hydrolase enzyme be inhibited or suppressed in such a manner that they cannot further catalyze the breakdown of starchy foodstuffs and beverages for subsequent utilization by the body and thus further promoting or worsening of the condition being treated.

While it was proposed heretofore to inhibit various amylases of the digestive tract or pancreas, for example, by the use of various substances, such as, low and high molecular weight organic substances, a distinct disadvantage of these proposed substances, as well as others known in the art is that either the inhibition of amylases is non-specific or that the inhibiting activity of the substance is slight, especially with respect to pancreatic amylases except at very high ratios of inhibitor to enzyme.

RELATIONSHIP TO COPENDING APPLICATION

U.S. Pat. Application Ser. No. 213,066, filed Dec. 28, 1971, entitled GLYCOSIDE-HYDROLASE ENZYME INHIBITORS discloses that microorganisms of the order Actinomycetales form inhibitors for glycoside-hydrolases, and in particular inhibitors for glycoside-hydrolases of preferentially carbohydrate-splitting enzymes of the digestive tract. One group of these inhibitors is relatively heat-stable and stable to acid and alkali at room temperature. Chemically speaking, these inhibitors belong to the class of the oligosaccharides or polysaccharides or their derivatives.

Thus, for example in Examples 28-38 of the aforesaid application describes the isolation of such an amylase inhibitor derived from the Actinoplanaceae strain CBS 961.70 belonging to the order Actinomycetales. The culture solutions resulting from fermentations of this strain under optional conditions contain about 30,000-40,000 AIU/ml., and the purest inhibitors isolated therefrom possess specific activities of 3-8 × 10⁶ amylase inhibitor units (AIU/g.).

THE PRESENT INVENTION

It has now been discovered that by the use of certain variants or mutants of the Actinoplanaceae strain CBS 961.70, namely the new strain CBS 614.71 and its mutants and variants, in conjunction with nutrient solutions of high starch content, culture broths containing 100,000–110,000 AIU/ml can be obtained.

The invention, accordingly, provides a novel process for the production of an amylase inhibitor which comprises culturing a microorganism of the family Actinoplanaceae, Strain CBS 961.70, a mutant or variant thereof, in a nutrient culture medium of high starch content under aerobic conditions for a period of time sufficient for the production of said amylase inhibitor and separating said amylase inhibitor from said nutrient culture medium.

As used herein, the expression "a mutant or variant" of Strain CBS 614.71 is defined as strains derived from Strain CBS 614.71 by mutations, as by bombardment with mutagenic radiation, or natural variation and variants or mutants produced from the parent strain CBS 961.70 alongside Strain CBS 614.71 by the method defined below.

This invention also provides a method of producing mutants and variants from Strain CBS 614.71 comprising:

i. distributing cells of Strain CBS 961.70 on nutrient agar, for example by plating-out;

ii. incubating the agar and cells for a plurality of days, preferably at 28°C., to produce separate colonies;

(iii). trans-inoculating the colonies individually and selecting therefrom cells having amylase-inhibiting properties.

The yield of this new strain and its variants and mutants can be increased in a known manner if the culture is exposed to mutagens before plating-out.

In carrying out the process of the invention, the pH of the fermentation medium is not necessarily a critical feature of the invention and but, preferably, a substantially neutral pH value should be maintained in the fermentation medium to this end a pH value in the range of from 5–8 will suffice. The amylase inhibitor produced under these conditions can be directly adsorbed onto activated charcoal from the culture solution and subsequently desorbed with aqueous alcohols or acetone especially at acid pH values of 1–3. It has been observed, further, that at acid pH values specified above desorption of the inhibiting principle is substantially complete while very strong adsorption of the dyestuffs, which contaminate the culture broths, takes place on activated charcoal. As a result of this technique inhibitor solutions of higher specific activity can be obtained by such a preliminary adsorption and removal of the dyestuff contaminants in the culture solution at acid pH values of from 1–3. This aspect of the invention is amply demonstrated in FIG. 1 of the drawing which illustrates the adsorption onto activated charcoal of the amylase inhibitor and of the brown dyestuffs (measured as the extinction at 550 nm) from the culture solution of CBS 614.71 at acid and neutral pH values within the ranges set forth above. In FIG. 1, the curves 1 and 2 represent the activities of the culture solutions, in AIU/ml on the righthand, y-axis, at pH values of 2.1 and 6.5 respectively after treatment with the amounts of activated charcoal, in grams, indicated on the x-axis. Curves 3 and 4 of FIG. 1 represent the extinctions at 550 nm on the left-hand, y-axis, at pH values of 6.5 and 2.1 respectively after treatment with the amounts of activated charcoal, in grams, indicated on the x-axis.

The new strain and its variants and mutants obtained as described above do not necessarily form more amylase inhibitor than the parent strain in all types of nutrient solutions. However, it has been found that particularly high yields of amylase inhibitor are formed if 3% or more of starch is included as a source of carbon in all of the nutrient solution. Particularly high yields are obtained with starch contents in the range of from about 4–6%.

Thus, for example, if fermentation of the culture is carried out for 3 days at 28°C. in a nutrient solution which, in addition to 2% of starch, also contains 1% of glucose, 0.5% of casein hydrolysate, 1% of yeast extract and 0.4% of $CaCO_3$, Strain CBS 961.70 yields a culture broth which contains 30–40,000 AIU/ml, and Strain CBS 614.71 yields a culture broth which contains 50–60,000 AIU/ml. Whereas, however, a nutrient solution having the composition of 5% of starch, 1% of yeast extract and 0.2% of $K_2HPO_4$, on the other hand, fermented for 3 days with Strain CBS 961.70 yields a culture containing 50-60,000 AIU/ml and with Strain CBS 614.71 yields 100–130,000 AIU/ml.

The yield of amylase inhibitor depends on the starch content. Up to about 5.5–6% of starch in the nutrient solution the content of amylase inhibitor increases. At higher concentrations the nutrient solutions become too viscous so that other factors, for example the poor supply of oxygen during the fermentation, reduce the yield.

The remaining constituents of the nutrient solution can vary greatly and the invention is not limited to any particular such constituents. For example, instead of the nitrogen sources of casein hydrolysate or yeast extract it is entirely possible to use only the corresponding amount of yeast extract or casein hydrolysate, or to replace both by other sources of nitrogen such as, for example, peptone.

The nutrient solution should also desirably contain a buffer system, which may be of any suitable compositions. A buffer system is only necessary to ensure that the pH value during the fermentation remains within physiological limits, that is to say between 5.0 and 8.5, preferably between 6.0 and 7.8. This can also be achieved by automatic addition of acids and alkalis. For example the buffer system may, but need not, consist of the initial mixture, $CaCO_3$, and potassium phosphate.

The addition of sugars, such as glucose, can accelerate the fermentation, especially the growth development, when added in small concentrations and can be added to the nutrient solutions as desired.

A preferred mode of producing highly active inhibitors by the process of the invention comprises fermenting Strain CBS 614.71 in a nutrient solution of 5% of starch, 1% of yeast extract and 0.2% of $K_2HPO_4$ for 3 days at 28°C. in shaking flasks of fermenters. After completion of the fermentation, the entire brown-colored batch is adjusted to pH 1–3, preferably 2–2.5, with half-concentrated $HNO_3$, and in order to decolorize it 2–10 g, preferably 5 g, of activated charcoal are added to each liter of culture solution. Thereafter the mycelium and the active charcoal are separated off by centrifuging or filtration, if necessary with the aid of a filtration auxiliary, and from the clear, light yellow supernatant liquid or filtrate the activity is isolated, after neutralization with ammonia, by concentration and fractional precipitation with alcohol or by adsorption on active charcoal. For this, the neutralized filtrate is treated with 0.3–1.5 g, preferably 0.75–1 g of active charcoal per $10^6$ AIU and the mixture is stirred for 10–120 minutes, preferably 20–30 minutes, at room temperature and filtered - if appropriate, with the aid of filtration auxiliaries. The amylase inhibiting principle is desorbed from the charcoal residue by means of 30–60% strength, preferably 50% strength, ethanol or 30–60% strength, preferably 50% strength, dioxane or 20–50% strength, preferably 35% strength, acetone, preferably at acid pH values of 2–3.

To obtain the amylase inhibitor, the Strain CBS 614.71 listed above is cultured in the nutrient solutions described above. After 1 to 10 days incubation at 15°–60°C., preferably 24°–50°C., in a shaking flask or in fermenters of different size, the mycelium is separated from the culture solution and, depending on the occurrence of the inhibitor, the active principle is concentrated using the culture solution and/or the mycelium or both.

The amylase inhibitor is obtained from the culture broths by lyophilization or precipitation with salts or watersoluble organic solvents (such as, for example, lower alcohols and ketones).

The inhibitors are obtained from the mycelia by extraction with organic solvents, such as, for example, alcohols, ketones, ethers, esters and sulfoxides.

For this purpose, the fermentation batch is centrifuged at 3,000–20,000 revolutions per minute, preferably 6,000–10,000 revolutions per minute, for 10–60 minutes, preferably 30 minutes, or is filtered, preferably under pressure and with the help of filter aids, such as, for example, Claricel, and is thus separated into culture broth and mycelium residue.

The inhibitor can be isolated from the particular culture broth in various ways:

a. Concentration of the culture broth under reduced pressure (10–50 mm Hg) at bath temperatures of 20°–100°C., preferably 40–80°C., to approximately 1/5 to 1/50 of the initial volume. The concentrated extract is filtered or centrifuged and the clear filtrate (or the clear supernatant liquid) is lyophilized, if required after prior desalination.

b. Precipitation of the inhibitors from the culture broth or from the culture broths concentrated according to (a) above by adding water-soluble organic solvents, such as, for example, alcohols or ketones, preferably methanol, ethanol, or acetone, up to a content of 60-90%. Since inactive concomitant substances are precipitated at low concentration of solvents, this precipitation process is particularly suitable for fractional precipitation to remove undesired concomitant substances.

c. Salting-out of the inhibitor from the extracts or from the extracts concentrated according to (a) above, for example, with ammonium sulfate, sodium chloride and the like. The precipitate formed is collected by centrifuging or filtering and is either directly washed with acetone and ether and dried in vacuo or redissolved in water, dialyzed and lyophilized.

In addition to the inhibitor, undesired concomitant substances are frequently present in the culture broths. These concomitant substances can be separated off in various ways, for example, by denaturing the concomitant substances by means of heat in the case of inhibitors which are heat-stable, or by dialysis through appropriate membranes in the case of low molecular inhibitors, in which case the undesired concomitant substances are retained by the membrane, or by fractional precipitation as discussed in (b) above.

The inhibitors are obtained from the mycelium by repeated extraction of the mycelium with organic solvents, preferably two extractions of 10–20 minutes with 3–5 volumes of acetone (relative to the moist mycelium volume) and subsequent single extraction of 5–10 minutes with ether. The mycelium extracted in this way is dried in vacuo and subsequently extracted for 2–8 hours with 3–10 parts by weight of dimethyl sulfoxide, while stirring, and thereafter centrifuged at 10,000 to 20,000 revolutions per minute. The acetone extracts and ether extracts are concentrated to dryness in vacuo and taken up with the dimethyl sulfoxide (DMSO) extract.

Instead of extracting the dry mycelium powder with dimethyl sulfoxide (DMSO), it can also be extracted over a longer period, preferably 12-24 hours, with water or dilute electrolyte solutions.

To determine the efficacy of the amylase inhibitor produced in accordance with the invention, samples are obtained in accordance with one or more of the recovery procedures enumerated above and tested in accordance with the procedure described below.

AMYLASE TEST

One amylase inhibitor unit (1 AIU) is defined as the amount of inhibitor which inhibits two amylase units to the extent of 50%. One amylase unit (AU) is the amount of enzyme which in one minute, under the test conditions indicated below, splits 1 $\mu$ equivalent of glucosidic bonds in the starch. The $\mu$ equivalent of split bonds are determined colorimetrically as $\mu$ equivalent of reducing sugars formed, by means of dinitrosalicylic acid, and are quoted as $\mu$ equivalent of maltose equivalents with the aid of a maltose calibration curve.

To carry out the test, 0.1 ml of amylase solution (20-22 AU/ml) are mixed with 0-10 $\mu$ g of inhibitor or 0-20 $\mu$ l of the inhibitor solution to be tested in 0.4 ml of 0.02 M sodium glycerophosphate buffer/0.001 M of $CaCl_2$ at pH 6.9 and the mixture is equilibrated for about 10-20 minutes in a water bath at 35°C. It is then incubated at 35°C. for 5 minutes with 0.5 ml of a 1% strength starch solution (soluble starch of Messrs. Merck, Darmstadt, No. 1252) which has been prewarmed to 35°C. and then mixed with 1 ml of dinitrosalicylic acid reagent (according to P. Bernfeld in Colowick-Kaplan, Meth. Enzymol., Volume 1, page 149). To develop the color, the batch is heated for 5 minutes on a boiling water bath, then cooled and mixed with 10 ml of distilled water. The extinction at 540 nm is measured against an appropriately composed blank without amylase.

For evaluation, the amylase activity which is still present after addition of inhibitor is read from a previously recorded amylase calibration curve and the percentage inhibition of the amylase employed is calculated therefrom. The percentage inhibition is plotted as a function of the quotient:

$\mu$g inhibitor*/AU**

* relative to dry substance
** AU in the uninhibited batch of the same series and the 50% inhibition point is read from the curve and converted to AIU/mg of inhibitor.

It has now been found that amylase inhibitor, according to the invention, obtained and isolated in accordance with the procedures discussed above, considerably reduce alimentary hyperglycemia, hyperinsulinemia and hypoglycemia after dosing rats and/or man with boiled and non-boiled starch and are, therefore, suitable for use as therapeutic agents for the indications, obesity, adiposity, hyperlippidemia (atherioscleroris), diabetes, pre-diabetes, gastritis, gastric ulcer, duodenal ulcer, and caries as previously discussed.

The present invention, therefore, provides a pharmaceutical composition containing, as the active ingredient, an amylase inhibitor of the invention in admixture with a liquid diluent other than a solvent of a molecular weight less than 200 (preferably less than 350) except in the presence of a surface active agent.

The invention further provides a pharmaceutical composition containing as active ingredient the amylase inhibitor of the invention in the form of a sterile or isotonic aqueous solution.

The invention also provides a medicament in dosage unit form comprising the amylase inhibitor of the invention either alone or in admixture with a diluent.

The invention also provides a medicament in the form of tablets, (including lozenges and granules), dragees, capsules, pills, ampoules and suppositories comprising the amylase inhibitor of the invention either alone or in admixture with a diluent.

"Medicament" as used herein means physically discrete coherent portions suitable for medical administration. "Medicament in dosage unit form" as used herein means physically discrete coherent portions suitable for medical administration each containing a unit dose or a multiple (up to four times) or submultiple [down to a fortieth (1/40)] of a unit dose of the inhibitor of the invention. Whether the medicament contains a unit dose or, for example, a half (1/2), a third (1/3), or a quarter (1/4), of a unit dose will depend on whether the medicament is to be administered once, for example, twice, three times or four times a day, respectively.

A unit dose is the amount of inhibitor to be taken on one occasion.

The pharmaceutical compositions according to the invention may, for example, take the form of gels, pastes (e.g. toothpastes), creams, chewing-gums, suspensions, solutions and emulsions of the active ingredient in aqueous or non-aqueous diluents, syrups, granules or powders.

The diluents to be used in pharmaceutical composition (e.g. granulates) adapted to be formed into tablets, dragees, capsules, and pills include the following: (a) fillers and extenders, e.g., starch, sugars, mannitol, and silicic acid; (b) binding agents, e.g., carboxymethyl cellulose and other cellulose derivatives, alginates, gelatine, and polyvinyl pyrrolidone; (c) moisturizing agents, e.g., glycerol; (d) disintegrating agents, e.g., agar-agar, calcium carbonate, and sodium bicarbonate, (e) agents for retarding dissolution, e.g., paraffin; (f) resorption accelerators, e.g., quaternary ammonium compounds; (g) surface active agents. e.g., cetyl alcohol, glycerol monostearate; (h) adsorptive carriers, e.g., kaolin and bentonite; (i) lubricants, e.g., talc, calcium and magnesium stearate, and solid polyethylene glycols; (j) elastomeric binders such as chicle.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the abovementioned diluents.

The diluents to be used in pharmaceutical compositions adapted to be formed into suppositories can, for example, be the usual water-soluble or water-insoluble diluents, such as polyethylene glycols and fats [e.g., cocoa oil and high esters (e.g., $C_{14}$-alcohol and $C_{16}$-fatty acid)] or mixtures of these diluents.

The pharmaceutical compositions which are pastes, creams, and gels can, for example, contain the usual diluents, e.g., animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders can, for example, contain the usual diluents, e.g., lactose, talc, silicic acid, aluminum hydroxide, calcium silicate, and polyamide powder or mixtures of these substances.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g., peppermint oil and eucalyptus oil) and sweetening agents (e.g., saccharin). In particular, chewing-gums and toothpastes will contain flavoring agents.

The pharmaceutical compositions according to the invention preferably contain about 0.1 to 99.5, more preferably from about 0.5 to 95% of the inhibitor by weight of the total composition.

In addition to an inhibitor of the invention, the pharmaceutical compositions according to the invention can also contain other pharmaceutically active compounds. They may also contain a plurality of different inhibitors of the invention. Particular examples of such other pharmaceutically active compounds are oral antidiabetic agents such as $\beta$-cytotropic sulfonyl-urea derivatives and biguanides which influence the blood sugar level.

The diluent in the medicament of the present invention may be any of these mentioned above in relation to the pharmaceutical compositions of the present invention. Such medicament may include solvents of molecular weight less than 200 as sole diluent.

The discrete coherent portions constituting the medicament according to the invention (whether in dosage unit form or not) may be, for example, any of the following: tablets (including lozenges and granules), pills, dragees, capsules, suppositories, and ampoules. Some of these forms may be made up for delayed release of the inhibitor. Some, such as capsules, include a protective envelope which renders the portions of the medicament physically discrete and coherent.

It is envisaged that the inhibitor will be administered perorally. Preferred medicaments are, therefore, those adapted for peroral administration, such as tablets, dragees, and portions of chewing-gum.

The following examples will serve to illustrate the practice of the invention in the production of the amylase inhibitor from CBS Strain 614.71, the recovery of the amylase inhibitor and its utility in rats and/or man.

EXAMPLE 1

If a 1 liter Erlenmeyer flask containing 120 ml of a nutrient solution of the composition 2% of starch, 1% of glucose, 0.5% of casein hydrolysate, 1.0% of yeast extract and 0.4% of $CaCO_3$ (sterilization: 30 minutes at 121°C., pH adjusted to 7.2, before sterilization, by means of KOH) is inoculated with 1 ml of a pre-culture of Strain CBS 614.71 (obtained in a nutrient solution having the composition 3% of glycerine, 3% of soya flour and 0.2% of $CaCO_3$, sterilization: 30 minutes at 121°C., pH after sterilization 7.2) and is incubated in a rotary shaking machine at 28°C., a culture broth which contains 55,000 AIU/ml is obtained after 3 days fermentation.

EXAMPLE 2

If the procedure of Example 1 is followed but with a nutrient solution having the composition 5% of starch, 1.0% of yeast extract and 0.2% of $K_2HPO_4$, a culture broth which contains 108,000 AIU/ml is obtained.

EXAMPLE 3

If a nutrient solution having the composition 4% of starch and 0.7% of yeast extract, is inoculated in accordance with Example 1 with Strain CBS 614.71, a culture broth containing 80,000 AIU/ml is obtained after 3 days fermentation.

EXAMPLE 4

If a nutrient solution having the composition 5% of starch, 1.0% of yeast extract and 0.4% of $K_2HPO_4$ is inoculated according to Example 1 with Strain CBS 614.71, a culture broth containing 105,000 AIU/ml is obtained after 4 days fermentation.

EXAMPLE 5

If a nutrient solution having the composition 6% of starch, 1.3% of yeast extract and 0.2% of $K_2HPO_4$ is inoculated in accordance with Example 1 with Strain CBS 614.71, a culture broth containing 120,000 AIU/ml is obtained after 4 days fermentation.

EXAMPLE 6

If a glass fermenter containing 8 liters of nutrient solution according to Example 2 is inoculated with a 3 day-old culture from a shaking flask and incubated with thorough stirring and aeration for 3 days at 28°C., a culture broth which contains 105,000 AIU/ml is obtained.

EXAMPLE 7

6 Liters of fermentation broth ($105 \times 10^6$ AIU/liter, total activity $630 \times 10^6$ AIU) produced as described in Example 6 are cooled to 20°C., adjusted to pH 2.5 with half-concentrated $HNO_3$, mixed with 30 g of Carboraffin active charcoal and stirred for 10 minutes. Thereafter the mixture is centrifuged for 15 minutes at 10,000 rpm and the clear, light yellow supernatant liquid (5.1 liters, $100 \times 10^6$ AIU/liter, total activity $510 \times 10^6$ AIU) is neutralized with ammonia ($NH_3$) and then concentrated to 500 ml ($970 \times 10^6$ AIU/liter, total activity $485 \times 10^6$ AIU). The 500 ml of concentrate were stirred for 45 minutes with 200 g of Amberlite IRA 410 resin Cl$^-$ form, filtered off and treated with 4/5 volume = 400 ml of methanol in order to precipitate the bulk of the higher-molecular starch degradation products (together with active charcoal remnants still present). The material is centrifuged for 5 minutes at 5,000 rpm. The 850 ml of supernatant liquid ($450 \times 10^6$ AIU/liter, total activity $380 \times 10^6$ AIU) are added dropwise, with vigorous stirring, to 4 liters of dry spirit. The white flocculent precipitate is filtered off, washed 3 times with dry spirit and twice with ether and dried in vacuo at 50°C. Yield: 36 g of a white powder of $10 \times 10^6$ AIU/g (total activity $360 \times 10^6$ AIU) = 57% yield (relative to activity.

EXAMPLE 8

2 Liters of fermentation broth produced as described in Example 6 ($100 \times 10^6$ AIU/liter, total activity $200 \times 10^6$ AIU) are adjusted to pH 2.5 with half-concentrated $HNO_3$ and 10 g of Carboraffin active charcoal added. After stirring for 10 minutes, the mycelium and the charcoal are sedimented at 15,000 rpm in 20 minutes. The clear supernatant liquid (1.6 liters, $95 \times 10^6$ AIU/liter, total activity $152 \times 10^6$ AIU) is neutralized with ammonia, then mixed with 120 g of active charcoal and stirred for 1 hour. Thereafter 60 g of Clarcell are added as a filter aid and the mixture is thereafter filtered. The charcoal residue is washed with 500 ml of water and 500 ml of 10% strength ethanol and subsequently twice mixed with 500 ml at a time of 35% strength acetone, which had beforehand been adjusted to pH 2.5 with HCl, and stirred for 20 minutes. After stirring, the mixture is filtered and the filtrates are combined (900 ml, $120 \times 10^6$ AIU/liter, total activity $110 \times 10^6$ AIU). The desorbate is neutralized with ammonia ($NH_3$) and concentrated to 50 ml on a rotary evaporator at ~20 mm Hg and subjected to a preliminary precipitation with 40 ml of methanol with stirring (the precipitate being discarded) and the filtrate is added dropwise to 500 ml of dry spirit while stirring vigorously. The precipitate is filtered off, washed with ethanol and ether and dried in vacuo at room temperature. Yield: 4.9 g with $14 \times 10^6$ AIU/g $\cong$ 34% yield, relative to the activity of the starting solution.

EXAMPLE 9

Experimental Technique for Demonstrating the Action of Amylase Inhibitors in Rats and Man To produce an alimentary hyperglycaemia after administration of starch, rats ($n = 6$) are given 1 g of boiled starch/kg, orally. Groups of 6 other rats receive, additionally to the starch, the amylase inhibitor from Example 7, in the indicated dosage. The blood glucose is determined, in the indicated time intervals after administration of starch, in the blood from the retro-orbital venous plexus by means of an autoanalyzer [Technicon, according to Hoffman; J. Biol. Chem. 120, 51 (1937)].

To produce an alimentary hyperglycaemia and hyperinsulinaemia in man ($n = 7–8$) 60 g of boiled starch are administered. The blood glucose is determined immediately before the beginning of the experiment and in short intervals thereafter, as indicated above, in the capillary blood of the fingertip. In further experiments, the active compound is added to the starch suspension.

Insulin determinations were carried out radioimmunilogically, based on the double antibody method of Hales and Randle [Biochem. J. 88, 137 (1963)] in the serum from venous blood.

TABLE 1

Accompanying Example 9
Average blood glucose in mg/100 ml ± ls of fasting rats at various times after oral administration of starch ± amylase inhibitor from Example 7.

|  | 5 | 10 | 15 |
|---|---|---|---|
| Control without starch | 67 ± 4.9 | 74 ± 13 | 69 ± 5.0 |
| Control with starch | 111 ± 7.2 | 128 ± 9.1 | 142 ± 6.5 |
| Starch + 0.02 mega-AIU/kg | 105 ± 8.8 | 111 ± 8.2 | 119 ± 8.6 |
| Starch + 0.05 mega-AIU/kg | 100 ± 9.1 | 101 ± 6.2 | 111 ± 5.5 |
| Starch + 0.12 mega-AIU/kg | 86 ± 8.5 | 81 ± 3.5 | 97 ± 9.4 |
| Starch + 0.20 mega-AIU/kg | 79 ± 4.7 | 77 ± 7.1 | 87 ± 5.9 |

|  | 20 | 30 | 45 minutes |
|---|---|---|---|
| Control without starch | 68 ± 3.6 | 64 ± 8.1 | 55 ± 5.9 |
| Control with starch | 132 ± 8.7 | 132 ± 7.5 | 109 ± 8.1 |
| Starch + 0.02 mega-AIU/kg | 118 ± 7.6 | 108 ± 7.3 | 100 ± 4.7 |
| Starch + 0.05 mega-AIU/kg | 107 ± 5.3 | 99 ± 7.9 | 87 ± 10 |
| Starch + 0.12 mega-AIU/kg | 81 ± 7.8 | 82 ± 8.9 | 66 ± 4.8 |
| Starch + 0.20 mega-AIU/kg | 85 ± 4.5 | 70 ± 4.6 | 70 ± 2.5 |

Legend:
------- $P < 0.05$
——— $P < 0.01$
======= $P < 0.001$ against control with starch

TABLE 2

Accompanying Example 9
Average blood glucose in mg/100 ± ls of fasting test persons (T.P.) before oral administration (= 0) and at various times after oral administration, of 60 g of starch ± amylase inhibitor from Example 7.

|  | 0 | 15 | 30 | 45 |
|---|---|---|---|---|
| Control with Starch | 96 ± 13 | 110 ± 19 | 159 ± 21 | 154 ± 23 |
| Starch + 0.3 mega-AIU/T.P. | 99 ± 10 | 102 ± 15 | 132 ± 14 | 128 ± 11 |
| Starch + 0.6 mega-AIU/T.P. | 88 ± 4.8 | 101 ± 6.3 | 108 ± 6.2 | 100 ± 8.5 |
| Starch + 1.2 mega-AIU/T.P. | 93 ± 9.5 | 100 ± 11 | 108 ± 8.3 | 102 ± 7.3 |
|  | 60 | 90 | 120 | 180 minutes |
| Control with starch | 131 ± 34 | 99 ± 21 | 85 ± 15 | 80 ± 14 |
| Starch + 0.3 mega-AIU/T.P. | 116 ± 15 | 98 ± 6.1 | 92 ± 12 | 86 ± 11 |
| Starch + 0.6 mega-AIU/T.P. | 95 ± 8.6 | 86 ± 6.4 | 78 ± 7.3 | 93 ± 6.4 |
| Starch + 1.2 mega-AIU/T.P. | 98 ± 9.8 | 87 ± 8.5 | 88 ± 7.3 | 90 ± 6.2 |

Legend:
------- $P < 0.05$
——— $P < 0.01$
====== $P < 0.001$ against control with starch

TABLE 3

Accompanying Example 9
Average insulin values in μU/ml of serum of fasting test persons (T.P.) before oral administration (= 0) and at various times after oral administration, of starch ± active compound from Example 7.

|  | 0 | 15 | 30 | 45 |
|---|---|---|---|---|
| Control with starch | 10 ± 2.0 | 26 ± 14 | 64 ± 29 | 59 ± 22 |
| Starch + 0.3 mega-AIU/T.P. | 11 ± 1.9 | 18 ± 4.6 | 29 ± 8.8 | 26 ± 10 |
| Starch + 0.6 mega-AIU/T.P. | 11 ± 3.3 | 21 ± 6.0 | 18 ± 6.8 | 17 ± 7.4 |
| Starch + 1.2 mega-AIU/T.P. | 8 ± 3.0 | 12 ± 5.9 | 13 ± 7.2 | 10 ± 4.7 |
|  | 60 | 90 | 120 | 180 mins. |
| Control with starch | 31 ± 20 | 19 ± 14 | 12 ± 6.5 | 10 ± 5.2 |
| Starch + 0.3 mega-AIU/T.P. | 22 ± 11 | 15 ± 5.3 | 14 ± 3.1 | 11 ± 2.4 |
| Starch + 0.6 mega-AIU/T.P. | 14 ± 6.8 | 13 ± 3.7 | 11 ± 3.4 | 10 ± 2.5 |
| Starch + 1.2 mega-AIU/T.P. | 8 ± 2.9 | 8 ± 2.9 | 9 ± 3.3 | 6 ± 3.0 |

Legend:
------- $P\ 0.05$
——— $P\ 0.01$
====== $P\ 0.001$ against control with starch

What is claimed is:

1. A pharmaceutical composition comprising an admixture of a pharmaceutical carrier and an effective amylase inhibiting amount of an amylase inhibitor active ingredient prepared in accordance with a process which comprises culturing the microorganism Actinoplanaceae CBS 614.71 in a nutrient medium until a sufficient quantity of amylase inhibitor has been produced, and recovering the said amylase inhibitor from the resultant culture.

* * * * *